(12) United States Patent
Quintana

(10) Patent No.: US 11,324,173 B2
(45) Date of Patent: May 10, 2022

(54) PASILLA PEPPER SHP9018

(71) Applicant: Sakata Seed America, Inc., Morgan Hill, CA (US)

(72) Inventor: Juan M. Quintana, Guamuchil Sinaloa (MX)

(73) Assignee: Sakata Seed America, Inc., Morgan Hill, CA (US)

( * ) Notice: Subject to any disclaimer, the term of this patent is extended or adjusted under 35 U.S.C. 154(b) by 260 days.

(21) Appl. No.: 16/541,126

(22) Filed: Aug. 14, 2019

(65) Prior Publication Data

US 2021/0045309 A1  Feb. 18, 2021

(51) Int. Cl.
*A01H 5/10* (2018.01)
*A01H 6/82* (2018.01)

(52) U.S. Cl.
CPC ............... *A01H 5/10* (2013.01); *A01H 6/822* (2018.05)

(58) Field of Classification Search
None
See application file for complete search history.

(56) References Cited

PUBLICATIONS

Poehlman et al., 1995, Methods in Plant Breeding IV, Iowa State Press; selected pp. 157-180.*

* cited by examiner

*Primary Examiner* — Bratislav Stankovic
(74) *Attorney, Agent, or Firm* — Weatherly IP Solutions, LLC; Barbara Campbell

(57) ABSTRACT

One embodiment relates to seed and plants of pepper hybrid SHP9018. Another embodiment relates to the plants, seeds and tissue cultures of pepper hybrid SHP9018, and to methods for producing a pepper plant produced by crossing such plants with themselves, with another pepper plant, such as a plant of another genotype, or with vegetatively propagating said plant. Another embodiment further relates to seeds and plants produced by such crossing. Further embodiments relate to parts of such plants, including the fruit and gametes of such plants.

22 Claims, No Drawings

PASILLA PEPPER SHP9018

BACKGROUND

The embodiments recited herein relates to a novel and distinct pasilla hybrid pepper (*Capsicum annuum*) designated SHP9018, and to the seeds, plant parts, and tissue culture produced by that hybrid pepper. The embodiments further relate to food products produced from hybrid pepper SHP9018, such as, but not limited to, fruit, powders, sauces, and salsas. All publications cited in this application are herein incorporated by reference.

The foregoing examples of the related art and limitations related therewith are intended to be illustrative and not exclusive. Other limitations of the related art will become apparent to those of skill in the art upon a reading of the specification.

SUMMARY

It is to be understood that the embodiments include a variety of different versions or embodiments, and this Summary is not meant to be limiting or all-inclusive. This Summary provides some general descriptions of some of the embodiments, but may also include some more specific descriptions of other embodiments.

An embodiment provides a hybrid pepper designated SHP9018. Another embodiment relates to the seeds of hybrid pepper SHP9018, to the plants of hybrid pepper SHP9018 and to methods for producing a pepper plant produced by crossing hybrid pepper SHP9018 with itself or another hybrid pepper, and the creation of variants by mutagenesis or transformation of hybrid pepper SHP9018.

Any such methods using hybrid pepper SHP9018 are a further embodiment: selfing, backcrosses, hybrid production, crosses to populations, and the like. All plants produced using hybrid pepper SHP9018 as at least one parent are within the scope of the embodiments. Advantageously, hybrid pepper SHP9018 could be used in crosses with other, different pepper plants to produce first generation ($F_1$) pepper hybrid seeds and plants with superior characteristics.

Another embodiment provided for a plant of hybrid pepper comprising an added heritable trait is provided. The heritable trait may comprise a genetic locus that is, for example, a dominant or recessive allele. In another embodiment, a plant of hybrid pepper SHP9018 is defined as comprising a single locus conversion. In another embodiment, an added genetic locus confers one or more traits such as, for example, herbicide tolerance, insect tolerance, tolerance for bacterial, fungal, or viral disease, male fertility, male sterility, enhanced nutritional quality, modified carbohydrate metabolism, environmental stress tolerance, modified yield, and industrial usage. In further embodiments, the trait may be conferred by a naturally occurring gene introduced into the genome of a line by backcrossing, a natural or induced mutation, or a transgene introduced through genetic transformation techniques into the plant or a progenitor of any previous generation thereof. When introduced through transformation, a genetic locus may comprise one or more genes integrated at a single chromosomal location.

Another embodiment provides for regenerable cells for use in tissue culture of hybrid pepper SHP9018. The tissue culture may be capable of regenerating plants having all the physiological and morphological characteristics of the foregoing pepper plant, and of regenerating plants having substantially the same genotype as the foregoing pepper plant. The regenerable cells in such tissue cultures may be embryos, protoplasts, meristematic cells, callus, pollen, leaves, ovules, anthers, cotyledons, hypocotyl, pistils, roots, root tips, fruit, flowers, seeds, plant, petiole, or stems. Still a further embodiment provides for pepper plants regenerated from the tissue cultures of hybrid pepper SHP9018.

Another embodiment relates to a method of vegetatively propagating pepper plant SHP9018 comprising the steps of: (a) collecting tissue capable of being propagated from a SHP9018 plant; (b) cultivating said tissue to obtain proliferated shoots; and (c) rooting said proliferated shoots to obtain rooted plantlets.

Another embodiment provides for the pepper seeds and plants produced by a process that comprises crossing a first parent pepper plant with a second parent pepper plant, wherein at least one of the first or second parent pepper plants is a plant of hybrid pepper hybrid. In one embodiment of the invention, pepper seed and plants produced by the process are first generation ($F_1$) hybrid pepper seed and plants produced by crossing a plant in accordance with the embodiments, with another, distinct plant. Another embodiment further contemplates plant parts of such an $F_1$ hybrid pepper plant, and methods of use thereof. Therefore, further embodiments provide for an $F_1$ hybrid pepper plant and seed thereof.

Another embodiment provides for a method of producing a plant derived from hybrid pepper SHP9018, the method comprising the steps of: (a) preparing a progeny plant derived from hybrid pepper SHP9018, wherein said preparing comprises crossing a plant of hybrid SHP9018 with a second plant; and (b) crossing the progeny plant with itself or a second plant to produce a seed of a progeny plant of a subsequent generation. In further embodiments, the method may additionally comprise: (c) growing a progeny plant of a subsequent generation from said seed of a progeny plant of a subsequent generation and crossing the progeny plant of a subsequent generation with itself or a second plant; and repeating the steps for an additional 3-10 generations to produce a plant derived from hybrid pepper SHP9018. The plant derived from hybrid SHP9018 may be an inbred line, and the aforementioned repeated crossing steps may be defined as comprising sufficient inbreeding to produce the inbred line. In the method, it may be desirable to select particular plants resulting from step (c) for continued crossing according to steps (b) and (c). By selecting plants having one or more desirable traits, a plant derived from hybrid SHP9018 is obtained which possesses some of the desirable traits of the line/hybrid as well as potentially other selected traits.

Further embodiments provide for a method of producing food or feed comprising: (a) obtaining a plant of hybrid pepper SHP9018, wherein the plant has been cultivated to maturity, and (b) collecting at least one pepper from the plant.

In another embodiment, the first step in "crossing" comprises planting seeds of a first and second parent pepper plant, often in proximity so that pollination will occur for example, mediated by insect vectors. Alternatively, pollen can be transferred manually. Where the plant is self-pollinated, pollination may occur without the need for direct human intervention other than plant cultivation. A second step may comprise cultivating or growing the seeds of first and second parent pepper plants into plants that bear flowers. A third step may comprise preventing self-pollination of the plants, such as by emasculating the flowers (i.e., killing or removing the pollen). A fourth step for a hybrid cross may comprise cross-pollination between the first and second parent pepper plants. Yet another step comprises harvesting the seeds from at least one of the parent pepper plants. The harvested seed can be grown to produce a pepper plant or hybrid pepper plant.

Another embodiment provides for a method for developing a pepper plant in a plant breeding program, comprising applying plant breeding techniques to the plant, or plant part thereof, of pepper SHP9018, comprising crossing, recurrent selection, mutation breeding, wherein said mutation breeding selects for a mutation that is spontaneous or artificially induced, backcrossing, pedigree breeding, marker enhanced selection, haploid/double haploid production, or transformation to pepper plant SHP9018, or its parts, wherein application of said techniques results in development of a pepper plant.

Another embodiment provides for a method of introducing a mutation into the genome of pepper plant SHP9018, said method comprising mutagenesis of the plant, or plant part thereof, of pepper plant SHP9018, wherein said mutagenesis is selected from the group consisting of temperature, long-term seed storage, tissue culture conditions, ionizing radiation, chemical mutagens, or targeting induced local lesions in genomes, and wherein the resulting plant comprises at least one genome mutation.

Another embodiment provides for a method of editing the genome of pepper plant SHP9018, said method comprising editing the genome of the plant, or plant part thereof, of pepper plant SHP9018, wherein said method is selected from the group comprising zinc finger nucleases, transcription activator-like effector nucleases (TALENs), engineered homing endonucleases/meganucleases, and the clustered regularly interspaced short palindromic repeat (CRISPR)-associated protein9 (Cas9) system.

The pepper seed of SHP9018 may be provided as an essentially homogeneous population of pepper seed of pepper hybrid SHP9018. Essentially homogeneous populations of seed are generally free from substantial numbers of other seed.

Another embodiment provides for the genetic complement of hybrid pepper SHP9018. The phrase "genetic complement" is used to refer to the aggregate of nucleotide sequences, the expression of which sequences defines the phenotype of, in the present case, a pepper plant, or a cell or tissue of that plant. A genetic complement thus represents the genetic makeup of a cell, tissue or plant, and a hybrid genetic complement represents the genetic make-up of a hybrid cell, tissue or plant. Thus another embodiment provides for pepper plant cells that have a genetic complement in accordance with the pepper plant cells disclosed herein, and seeds and plants containing such cells.

As used herein, "at least one," "one or more," and "and/or" are open-ended expressions that are both conjunctive and disjunctive in operation. For example, each of the expressions "at least one of A, B and C," "at least one of A, B, or C," "one or more of A, B, and C," "one or more of A, B, or C" and "A, B, and/or C" means A alone, B alone, C alone, A and B together, A and C together, B and C together, or A, B and C together.

Various embodiments are set forth in the Detailed Description as provided herein and as embodied by the claims. It should be understood, however, that this Summary does not contain all of the aspects and embodiments, is not meant to be limiting or restrictive in any manner, and that embodiment(s) as disclosed herein is/are understood by those of ordinary skill in the art to encompass obvious improvements and modifications thereto.

In addition to the exemplary aspects and embodiments described above, further aspects and embodiments will become apparent by study of the following descriptions.

Definitions

In the description and tables herein, a number of terms are used. In order to provide a clear and consistent understanding of the specification and claims, including the scope to be given such terms, the following definitions are provided:

Cotyledon. A cotyledon is a type of seed leaf. The cotyledon contains the food storage tissues of the seed.

Embryo. The embryo is the small plant contained within a mature seed.

Gene. Gene refers to a segment of nucleic acid. A gene can be introduced into a genome of a species, whether from a different species or from the same species, using transformation or various breeding methods.

Hypocotyl. A hypocotyl is the portion of an embryo or seedling between the cotyledons and the root. Therefore, it can be considered a transition zone between shoot and root.

Locus. Locus or loci (plural) refers to a position in the genome for a gene, SNP, mutation, etc.

Plant Parts. Plant parts (or a pepper plant, or a part thereof) includes but is not limited to, regenerable cells in such tissue cultures may be embryos, protoplasts, meristematic cells, callus, pollen, anther, shoot, leaves, ovules, anthers, cotyledons, hypocotyl, pistils, roots, root tips, fruit, flowers, seeds, plant, petiole, or stems.

Quantitative Trait Loci (QTL). Quantitative trait loci (QTL) refer to genetic loci that control to some degree numerically representable traits that are usually continuously distributed.

Regeneration. Refers to the development of a plant from tissue culture.

RHS. RHS refers to the Royal Horticultural Society color reference.

Single Gene Converted (Conversion). Single gene converted (conversion) plants refers to plants which are developed by a plant breeding technique called backcrossing wherein essentially all of the desired morphological and physiological characteristics of a variety are recovered in addition to the single gene transferred into the variety via the backcrossing technique or via genetic engineering. By essentially all of the morphological and physiological characteristics, it is meant that the characteristics of a plant are recovered that are otherwise present when compared in the same environment, other than an occasional variant trait that might arise during backcrossing or direct introduction of a transgene.

Wall Thickness. Wall or flesh thickness refers to the diameter of the fruit wall. Wall thickness is measured by cutting the fruit in half longitudinally and measuring the thickness (mm) on the thinnest part of each side of the wall of each fruit. Wall thickness is important to both bell pepper growers and shippers because fruit having thick walls are more likely to ship better without the fruit wall cracking.

DETAILED DESCRIPTION

Hybrid pepper SHP9018 is a poblano pepper that is adapted to most areas in the United States. SHP9018 has a semi-spreading plant habit with fruit that is hot in pungency. Additionally, SHP9018 has intermediate resistance (IR) to

*Phytophthora capsica* (Pc) and Tobacco Mosaic Virus race 0 (TMV:0).

Hybrid pepper SHP9018 has shown uniformity and stability, as described in the following variety description information. Hybrid pepper SHP9018 was tested for uniformity and stability a sufficient number of generations with careful attention to uniformity of plant type and has been increased with continued observation for uniformity.

Hybrid pepper SHP9018 has the following morphologic and other characteristics based primarily on data collected in Ft. Myers, Fla.

TABLE 1

| VARIETY DESCRIPTION INFORMATION | |
|---|---|
| Characteristic | SHP9018 |
| General Fruit Type | Pasilla |
| Adaptation | Most U.S. Areas |
| Maturity-Transplant to Green Stage | 90 days |
| Maturity-Transplant to Red or Yellow Stage | 105 days |
| Maturity-Seedling to Green Stage | 115 days |
| Maturity-Seedling to Red or Yellow Stage | 150 days |
| Plant Habit | Semi-Spreading |
| Plant Attitude | Semi-Erect |
| Plant Height | 120.0 cm |
| Plant Width | 54.0 cm |
| Length of Stem From Cotyledons to 1st Flower | 19.5 cm |
| Length of Third Internode (from soil surface) | 290.0 mm |
| Basal Branches | Many (More than 3) |
| Branch Flexibility | Rigid |
| Stem Strength | Intermediate |
| Mature Leaf Shape | Lanceolate |
| Leaf Length | 92.0 mm |
| Leaf width | 40.0 mm |
| Petiole Length | 41.0 mm |
| Leaf and Stem Pubescence | Absent |
| Margin Undulation | Weak |
| Blistering | Weak |
| Leaf Color | Dark Green-Upper surface: RHS 147A (Yellow-Green), Lower surface: RHS 147B (Yellow-Green) |
| Number of Flowers Per Leaf Axil | 3 |
| Number of Calyx Lobes | 6 |
| Number of Petals | 6 |
| Flower Diameter | 23.0 mm |
| Corolla Color | White |
| Corolla Throat Markings | Absent |
| Anther Color | RHS N189A (Greyed-Green) |
| Style Length | Exceeds Stamen |
| Self-Incompatibility | Absent |
| Immature Fruit Color | Medium Green-Closest to but darker than RHS 139A (Green) |
| Mature Fruit Color | Brown |
| Pungency | Hot |
| Fruit Glossiness | Moderate |
| Surface Smoothness | Smooth |
| Fruit Position | Pendant |
| Calyx Shape | Cup-Shaped |
| Calyx Diameter | 19.0 mm |
| Fruit Length | 186.0 mm |
| Fruit Diameter at Calyx Attachment | 190.0 mm |
| Fruit Diameter at Mid-Point | 30.0 mm |
| Flesh Thickness at Mid-Point | 3.0 mm |
| Average Number of Fruit/Plant | 22 |
| Average Fruit Weight | 33.0 gm |
| Fruit Base Shape | Rounded |
| Fruit Apex Shape | Pointed |
| Fruit Shape | Elongated |
| Fruit Shape (Longitudinal Section) | Horn-Shaped |
| Fruit Shape (Cross Section) | Circular |
| Fruit Set | Scattered |
| Interloculary Grooves | Very Shallow |
| Average Number of Locules | 10 |
| Pedicel Length | 70.0 mm |
| Pedicel Thickness | 5.0 mm |
| Pedicel Shape | Curved |
| Pedicel Cavity | Absent |
| Seed Cavity Length | 172.0 mm |
| Seed Cavity Diameter | 25.0 mm |
| Placenta Length | 140.0 mm |
| Number of Seeds Per Fruit | 170 |
| Seed Color | Yellow |

TABLE 1-continued

VARIETY DESCRIPTION INFORMATION

| Characteristic | SHP9018 |
| --- | --- |
| Anthocyanin Presence in Seedling Hypocotyl | Absent |
| Anthocyanin Presence in Stem | Absent |
| Anthocyanin Presence in Node | Absent |
| Anthocyanin Presence in Leaf | Absent |
| Anthocyanin Presence in Pedicel | Absent |
| Anthocyanin Presence in Calyx | Absent |
| Anthocyanin Presence in Fruit | Absent |
| Disease Resistance | TMV:0, PC: IR |

Breeding With Hybrid Pepper SHP9018

The complexity of inheritance influences choice of the breeding method. Backcross breeding is used to transfer one or a few favorable genes for a highly heritable trait into a desirable variety. This approach has been used extensively for breeding disease-resistant varieties. Various recurrent selection techniques are used to improve quantitatively inherited traits controlled by numerous genes. The use of recurrent selection in self-pollinating crops depends on the ease of pollination, the frequency of successful hybrids from each pollination, and the number of hybrid offspring from each successful cross.

Promising advanced breeding lines are thoroughly tested and compared to appropriate standards in environments representative of the commercial target area(s) for three or more years. The best lines are candidates for new commercial varieties; those still deficient in a few traits may be used as parents to produce new populations for further selection.

These processes, which lead to the final step of marketing and distribution, is a time-consuming process that requires precise forward planning, efficient use of resources, and a minimum of changes in direction.

A most difficult task is the identification of individuals that are genetically superior, because for most traits the true genotypic value is masked by other confounding plant traits or environmental factors. One method of identifying a superior plant is to observe its performance relative to other experimental plants and to a widely grown standard variety. If a single observation is inconclusive, replicated observations provide a better estimate of its genetic worth.

The goal of pepper breeding is to develop new and superior pepper varieties and hybrids. The breeder initially selects and crosses two or more parental lines, followed by repeated selfing and selection, producing many new genetic combinations. The breeder can theoretically generate billions of different genetic combinations via crossing, selection, selfing and mutations.

Using Hybrid Pepper SHP9018 to Develop other Pepper Varieties

Pepper varieties such as hybrid pepper SHP9018 are typically developed for fresh consumption. However, pepper varieties such as hybrid pepper SHP9018 also provide a source of breeding material that may be used to develop new pepper varieties. Plant breeding techniques known in the art and used in a pepper breeding program include, but are not limited to, recurrent selection, bulk selection, mass selection, backcrossing, pedigree breeding, open pollination breeding, restriction fragment length polymorphism enhanced selection, genetic marker enhanced selection, making double haploids, transformation, and gene editing. These techniques can be used singularly or in combinations. The development of pepper varieties in a breeding program requires, in general, the development and evaluation of homozygous varieties. There are many analytical methods available to evaluate a new variety. The oldest and most traditional method of analysis is the observation of phenotypic traits, but genotypic analysis may also be used.

Additional Breeding Methods

One embodiment is directed to methods for producing a pepper plant by crossing a first parent pepper plant with a second parent pepper plant, wherein the first or second pepper plant is the pepper plant from hybrid pepper SHP9018. Further, both first and second parent pepper plants may be from hybrid pepper SHP9018. Any plants produced using hybrid pepper SHP9018 as at least one parent are also within the scope of the embodiments. These methods are well known in the art and some of the more commonly used breeding methods are described herein. Descriptions of breeding methods can be found in one of several reference books (e.g., Allard, Principles of Plant Breeding (1960); Simmonds, *Principles of Crop Improvement* (1979); Sneep, et al. (1979); Cooper, S. G., D. S. Douches and E. J. Grafius. (2004).

The following describes breeding methods that may be used with hybrid pepper SHP9018 in the development of further pepper plants. One such embodiment is a method for developing a hybrid pepper SHP9018 progeny plant in a pepper breeding program comprising: obtaining the pepper plant, or a part thereof, of hybrid pepper SHP9018, utilizing said plant, or plant part, as a source of breeding material, and selecting a hybrid pepper SHP9018 progeny plant with molecular markers in common with hybrid pepper SHP9018 and/or with morphological and/or physiological characteristics selected from the characteristics listed in Table 1. Breeding steps that may be used in the pepper plant breeding program include pedigree breeding, backcrossing, mutation breeding, and recurrent selection. In conjunction with these steps, techniques such as RFLP-enhanced selection, genetic marker enhanced selection (for example, SSR markers), and the making of double haploids may be utilized.

Another method involves producing a population of hybrid pepper SHP9018 progeny pepper plants, comprising crossing hybrid pepper SHP9018 with another pepper plant, thereby producing a population of pepper plants which derive 50% of their alleles from hybrid pepper SHP9018. A plant of this population may be selected and repeatedly selfed or sibbed with a hybrid pepper line resulting from these successive filial generations. One embodiment is the hybrid pepper produced by this method and that has obtained at least 50% of its alleles from hybrid pepper SHP9018.

One of ordinary skill in the art of plant breeding would know how to evaluate the traits of two plant varieties to determine if there is no significant difference between the two traits expressed by those varieties. For example, see, Fehr and Walt, *Principles of Variety Development*, pp.

261-286 (1987). Thus, embodiments include hybrid pepper SHP9018 progeny pepper plants comprising a combination of at least two hybrid pepper SHP9018 traits selected from the group consisting of those listed in Table 1 and a combination of traits listed in the Summary, so that said progeny pepper plant is not significantly different for said traits than hybrid pepper SHP9018 as determined at the 5% significance level when grown in the same environmental conditions. Using techniques described herein, molecular markers may be used to identify said progeny plant as a hybrid pepper SHP9018 progeny plant. Mean trait values may be used to determine whether trait differences are significant, and preferably the traits are measured on plants grown under the same environmental conditions. Once such a variety is developed, its value is substantial since it is important to advance the germplasm base as a whole in order to maintain or improve traits such as yield, disease tolerance, pest tolerance, and plant performance in extreme environmental conditions.

Progeny of hybrid pepper SHP9018 may also be characterized through their filial relationship with hybrid pepper SHP9018, as for example, being within a certain number of breeding crosses of hybrid pepper SHP9018. A breeding cross is a cross made to introduce new genetics into the progeny, and is distinguished from a self or a sib cross, which is made to select among existing genetic alleles. The lower the number of breeding crosses in the pedigree, the closer the relationship between hybrid pepper SHP9018 and its progeny. For example, progeny produced by the methods described herein may be within 1, 2, 3, 4, or 5 breeding crosses of hybrid pepper SHP9018.

Pedigree Breeding

Pedigree breeding starts with the crossing of two genotypes, such as hybrid pepper SHP9018 and another hybrid pepper having one or more desirable characteristics that is lacking or which complements hybrid pepper SHP9018. If the two original parents do not provide all the desired characteristics, other sources can be included in the breeding population. In the pedigree method, superior plants are selfed and selected in successive filial generations. In the succeeding filial generations, the heterozygous condition gives way to homogeneous varieties as a result of self-pollination and selection. Typically, in the pedigree method of breeding, five or more successive filial generations of selfing and selection is practiced: $F_1$ to $F_2$; $F_2$ to $F_3$; $F_3$ to $F_4$; $F_4$ to $F_5$; etc. After a sufficient amount of inbreeding, successive filial generations will serve to increase seed of the developed variety. Preferably, the developed variety comprises homozygous alleles at about 95% or more of its loci.

Backcross Breeding

Backcross breeding has been used to transfer genes for a simply inherited, highly heritable trait into a desirable homozygous variety or hybrid which is the recurrent parent. The source of the trait to be transferred is called the donor parent. After the initial cross, individuals possessing the phenotype of the donor parent are selected and repeatedly crossed (backcrossed) to the recurrent parent. The resulting plant is expected to have the attributes of the recurrent parent (e.g., variety) and the desirable trait transferred from the donor parent. This is also known as single gene conversion and/or backcross conversion.

The selection of a suitable recurrent parent is an important step for a successful backcrossing procedure. The goal of a backcross protocol is to alter or substitute a single trait or characteristic in the original variety. To accomplish this, a single gene of the recurrent variety is modified or substituted with the desired gene from the nonrecurrent parent, while retaining essentially all of the rest of the desired genetic, and therefore the desired physiological and morphological constitution of the original variety. The choice of the particular nonrecurrent parent will depend on the purpose of the backcross; one of the major purposes is to add some agronomically important trait to the plant. The exact backcrossing protocol will depend on the characteristic or trait being altered to determine an appropriate testing protocol. Although backcrossing methods are simplified when the characteristic being transferred is a dominant allele, a recessive allele may also be transferred. It may be necessary to introduce a test of the progeny to determine if the desired characteristic has been successfully transferred.

A backcross conversion of hybrid pepper SHP9018 occurs when DNA sequences are introduced through backcrossing, with hybrid pepper SHP9018 utilized as the recurrent parent. Both naturally occurring and transgenic DNA sequences may be introduced through backcrossing techniques. A backcross conversion may produce a plant with a trait or locus conversion in at least two or more backcrosses, including at least 2 crosses, at least 3 crosses, at least 4 crosses, at least 5 crosses, and the like. Molecular marker assisted breeding or selection may be utilized to reduce the number of backcrosses necessary to achieve the backcross conversion. For example, see, Frisch M. et al, "Marker-Assisted Backcrossing for Simultaneous Introgression of Two Genes" *Crop Science Society of America*, pp 1716-1725 (2001) and Openshaw, S. J., et al., "Marker-assisted Selection in Backcross Breeding, Proceedings Symposium of the Analysis of Molecular Data" *Crop Science Society of America*, Corvallis, Oreg. (August 1994), where it was demonstrated that a backcross conversion could be made in as few as two backcrosses.

The complexity of the backcross conversion method depends on the type of trait being transferred (single genes or closely linked genes as compared to unlinked genes), the level of expression of the trait, the type of inheritance (cytoplasmic or nuclear), and the types of parents included in the cross. It is understood by those of ordinary skill in the art that for single gene traits that are relatively easy to classify, the backcross method is effective and relatively easy to manage. Desired traits that may be transferred through backcross conversion include, but are not limited to, sterility (nuclear and cytoplasmic), fertility restoration, nutritional enhancements, drought tolerance, nitrogen utilization, low phytate, industrial enhancements, disease tolerance (bacterial, fungal, or viral), insect tolerance, and herbicide tolerance. In addition, an introgression site itself, such as an FRT site, Lox site, or other site specific integration site, may be inserted by backcrossing and utilized for direct insertion of one or more genes of interest into a specific plant variety. In some embodiments, the number of loci that may be backcrossed into hybrid pepper SHP9018 is at least 1, 2, 3, 4, or 5, and/or no more than 6, 5, 4, 3, or 2. A single locus may contain several transgenes, such as a transgene for disease tolerance that, in the same expression vector, also contains a transgene for herbicide tolerance. The gene for herbicide tolerance may be used as a selectable marker and/or as a phenotypic trait. A single locus conversion of site specific integration system allows for the integration of multiple genes at the converted loci.

The backcross conversion may result from either the transfer of a dominant allele or a recessive allele. Selection of progeny containing the trait of interest is accomplished by direct selection for a trait associated with a dominant allele. Transgenes transferred via backcrossing typically function as a dominant single gene trait and are relatively easy to classify. Selection of progeny for a trait that is transferred via a recessive allele requires growing and selfing each backcross generation to determine which plants carry the recessive alleles unless molecular markers are available to track the gene. Recessive traits may require additional progeny testing in successive backcross generations to confirm the presence of the locus of interest. The last backcross generation is usually selfed to give pure breeding progeny for the gene(s) being transferred, although a backcross conversion with a stably introgressed trait may also be maintained by further backcrossing to the recurrent parent with selection for the converted trait.

Along with selection for the trait of interest, progeny are selected for the phenotype of the recurrent parent. The backcross is a form of inbreeding, and the features of the recurrent parent are automatically recovered after successive backcrosses. Poehlman, "Breeding Field Crops" p. 204 (1987). Poehlman suggests from one to four or more backcrosses, but as noted above, the number of backcrosses necessary can be reduced with the use of molecular markers. Other factors, such as a genetically similar donor parent, may also reduce the number of backcrosses necessary. As noted by Poehlman, backcrossing is easiest for simply inherited, dominant, and easily recognized traits.

One process for adding or modifying a trait or locus in hybrid pepper SHP9018 comprises crossing hybrid pepper SHP9018 plants grown from hybrid pepper SHP9018 seed with plants of another hybrid pepper that comprise the desired trait or locus, selecting $F_1$ progeny plants that comprise the desired trait or locus to produce selected $F_1$ progeny plants, crossing the selected progeny plants with the hybrid pepper SHP9018 plants to produce backcross progeny plants, selecting for backcross progeny plants that have the desired trait or locus and the morphological characteristics of hybrid pepper SHP9018 to produce selected backcross progeny plants, and backcrossing to hybrid pepper SHP9018 three or more times in succession to produce selected fourth or higher backcross progeny plants that comprise said trait or locus. The modified hybrid pepper SHP9018 may be further characterized as having the physiological and morphological characteristics of hybrid pepper SHP9018 listed in Table 1 as determined at the 5% significance level when grown in the same environmental conditions and/or may be characterized by percent similarity or identity to hybrid pepper SHP9018 as determined by SSR markers. The above method may be utilized with fewer backcrosses in appropriate situations, such as when the donor parent is highly related or markers are used in the selection step. Desired traits that may be used include those nucleic acids known in the art, some of which are listed herein, that will affect traits through nucleic acid expression or inhibition. Desired loci include the introgression of FRT, Lox, and other sites for site specific integration, which may also affect a desired trait if a functional nucleic acid is inserted at the integration site.

In addition, the above process and other similar processes described herein may be used to produce first generation progeny pepper seed by adding a step at the end of the process that comprises crossing hybrid pepper SHP9018 with the introgressed trait or locus with a different pepper plant and harvesting the resultant first-generation progeny pepper seed.

Many single gene traits have been identified that are not regularly selected for in the development of a new variety but that can be improved by backcrossing techniques well-known in the art. Single gene traits may or may not be transgenic. Examples of these traits include, but are not limited to, herbicide tolerance, insect tolerance, tolerance for bacterial, fungal, or viral disease, male fertility, male sterility, enhanced nutritional quality, modified carbohydrate metabolism, modified yield, environmental stress tolerance, and industrial usage In addition to being used to create a backcross conversion, backcrossing can also be used in combination with pedigree breeding. As discussed previously, backcrossing can be used to transfer one or more specifically desirable traits from one variety, the donor parent, to a developed variety called the recurrent parent, which has overall good agronomic characteristics yet lacks that desirable trait or traits. However, the same procedure can be used to move the progeny toward the genotype of the recurrent parent, but at the same time retain many components of the nonrecurrent parent by stopping the backcrossing at an early stage and proceeding with selfing and selection. For example, a hybrid pepper may be crossed with another variety to produce a first generation progeny plant. The first generation progeny plant may then be backcrossed to one of its parent varieties to create a $BC_1$ or $BC_2$. Progeny are selfed and selected so that the newly developed variety has many of the attributes of the recurrent parent and yet several of the desired attributes of the nonrecurrent parent. This approach leverages the value and strengths of the recurrent parent for use in new pepper varieties.

Therefore, an embodiment of the present disclosure is a method of making a backcross conversion hybrid pepper SHP9018, comprising the steps of crossing a plant of hybrid pepper SHP9018 with a donor plant comprising a desired trait, selecting an $F_1$ progeny plant comprising the desired trait, and backcrossing the selected $F_1$ progeny plant to a plant of hybrid pepper SHP9018 to produce $BC_1$, $BC_2$, $BC_3$, etc. This method may further comprise the step of obtaining a molecular marker profile of hybrid pepper SHP9018 and using the molecular marker profile to select for a progeny plant with the desired trait and the molecular marker profile of hybrid pepper SHP9018. In one embodiment, the desired trait is a mutant gene, gene, or transgene present in the donor parent.

Recurrent Selection and Mass Selection

Recurrent selection is a method used in a plant breeding program to improve a population of plants. Hybrid pepper SHP9018 is suitable for use in a recurrent selection program. The method entails individual plants cross pollinating with each other to form progeny. The progeny are grown and the superior progeny selected by any number of selection methods, which include individual plant, half-sib progeny, full-sib progeny, and selfed progeny. The selected progeny are cross pollinated with each other to form progeny for another population. This population is planted and again superior plants are selected to cross pollinate with each other. Recurrent selection is a cyclical process and therefore can be repeated as many times as desired. The objective of recurrent selection is to improve the traits of a population. The improved population can then be used as a source of breeding material to obtain new varieties for commercial or breeding use, including the production of a synthetic variety. A synthetic variety is the resultant progeny formed by the intercrossing of several selected varieties.

Mass selection is a useful technique when used in conjunction with molecular marker enhanced selection. In mass selection, seeds from individuals are selected based on phenotype or genotype. These selected seeds are then bulked and used to grow the next generation. Bulk selection requires growing a population of plants in a bulk plot, allowing the plants to self-pollinate, harvesting the seed in bulk, and then using a sample of the seed harvested in bulk to plant the next generation. Also, instead of self-pollination, directed pollination could be used as part of the breeding program.

Mass and recurrent selections can be used to improve populations of either self- or cross-pollinating crops. A genetically variable population of heterozygous individuals is either identified, or created, by intercrossing several different parents. The plants are selected based on individual superiority, outstanding progeny, or excellent combining ability. The selected plants are intercrossed to produce a new population in which further cycles of selection are continued.

Mutation Breeding

Mutation breeding is another method of introducing new traits into hybrid pepper SHP9018. Mutations that occur spontaneously or are artificially induced can be useful sources of variability for a plant breeder. The goal of artificial mutagenesis is to increase the rate of mutation for a desired characteristic. Mutation rates can be increased by many different means including temperature, long-term seed storage, tissue culture conditions, radiation; such as X-rays, Gamma rays (e.g., cobalt 60 or cesium 137), neutrons, (product of nuclear fission by uranium 235 in an atomic reactor), Beta radiation (emitted from radioisotopes such as phosphorus 32 or carbon 14), or ultraviolet radiation (preferably from 2500 to 2900 nm), or chemical mutagens (such as base analogues (5-bromo-uracil)), related compounds (8-ethoxy caffeine), antibiotics (streptonigrin), alkylating agents (sulfur mustards, nitrogen mustards, epoxides, ethylenamines, sulfates, sulfonates, sulfones, lactones), azide, hydroxylamine, nitrous acid, or acridines. Once a desired trait is observed through mutagenesis the trait may then be incorporated into existing germplasm by traditional breeding techniques. Details of mutation breeding can be found in Fehr, "Principles of Variety Development," Macmillan Publishing Company (1993). In addition, mutations created in other pepper plants may be used to produce a backcross conversion of hybrid pepper SHP9018 that comprises such mutation.

Additional methods include, but are not limited to, expression vectors introduced into plant tissues using a direct gene transfer method, such as microprojectile-mediated delivery, DNA injection, electroporation, and the like. More preferably, expression vectors are introduced into plant tissues by using either microprojectile-mediated delivery with a biolistic device or by using *Agrobacterium*-mediated transformation. Transformant plants obtained with the protoplasm of the embodiments are intended to be within the scope of the embodiments.

Gene Editing Using CRISPR

Targeted gene editing can be done using CRISPR/Cas9 technology (Saunders & Joung, *Nature Biotechnology*, 32, 347-355, 2014). CRISPR is a type of genome editing system that stands for Clustered Regularly Interspaced Short Palindromic Repeats. This system and CRISPR-associated (Cas) genes enable organisms, such as select bacteria and archaea, to respond to and eliminate invading genetic material. Ishino, Y., et al. *J. Bacteriol.* 169, 5429-5433 (1987). These repeats were known as early as the 1980s in *E. coli*, but Barrangou and colleagues demonstrated that *S. thermophilus* can acquire resistance against a bacteriophage by integrating a fragment of a genome of an infectious virus into its CRISPR locus. Barrangou, R., et al. *Science* 315, 1709-1712 (2007). Many plants have already been modified using the CRISPR system, including *Capsicum annuum*. See for example, U.S. Application Publication No. WO2014068346 (Gyorgy et al., Identification of a *Xanthomonas euvesicatoria* resistance gene from pepper (*Capsicum annuum*) and method for generating plants with resistance), Martinelli, F. et al., "Proposal of a Genome Editing System for Genetic Resistance to Tomato Spotted Wilt Virus" *American Journal of Applied Sciences* 2014, and Noman, A. et al., "CRISPR-Cas9: Tool for Qualitative and Quantitative Plant Genome Editing" *Frontiers in Plant Science* Vol. 7 November 2016.

Gene editing can also be done using crRNA-guided surveillance systems for gene editing. Additional information about crRNA-guided surveillance complex systems for gene editing can be found in the following documents, which are incorporated by reference in their entirety: U.S. Application Publication No. 2010/0076057 (Sontheimer et al., Target DNA Interference with crRNA); U.S. Application Publication No. 2014/0179006 (Feng, CRISPR-CAS Component Systems, Methods, and Compositions for Sequence Manipulation); U.S. Application Publication No. 2014/0294773 (Brouns et al., Modified Cascade Ribonucleoproteins and Uses Thereof); Sorek et al., *Annu. Rev. Biochem.* 82:273-266, 2013; and Wang, S. et al., *Plant Cell Rep* (2015) 34: 1473-1476. Therefore, it is another embodiment to use the CRISPR system on hybrid pepper SHP9018 to modify traits and tolerances to pests, herbicides, and viruses.

Gene Editing Using TALENs

Transcription activator-like effector nucleases (TALENs) have been successfully used to introduce targeted mutations via repair of double stranded breaks (DSBs) either through non-homologous end joining (NHEJ), or by homology-directed repair (HDR) and homology-independent repair in the presence of a donor template. Thus, TALENs are another mechanism for targeted genome editing using SHP9018. The technique is well known in the art; see for example Malzahn, Aimee et al. "Plant genome editing with TALEN and CRISPR" *Cell & bioscience* vol. 7 21. 24 Apr. 2017.

Therefore, it is another embodiment to use the TALENs system on hybrid pepper SHP9018 to modify traits and resistances or tolerances to pests, herbicides, and viruses.

Other Methods of Genome Editing

In addition to CRISPR and TALENs, two other types of engineered nucleases can be used for genome editing: engineered homing endonucleases/meganucleases (EMNs), and zinc finger nucleases (ZFNs). These methods are well known in the art. See for example, Petilino, Joseph F. "Genome editing in plants via designed zinc finger nucleases" *In Vitro Cell Dev Biol Plant.* 51(1): pp. 1-8 (2015); and Daboussi, Fayza, et al. "Engineering Meganuclease for Precise Plant Genome Modification" in Advances in New Technology for Targeted Modification of Plant Genomes. Springer Science+Business. pp 21-38 (2015).

Therefore, it is another embodiment to use engineered nucleases on hybrid pepper SHP9018 to modify traits and resistances or tolerances to pests, herbicides, and viruses.

Introduction of a New Trait or Locus into Hybrid Pepper SHP9018

Hybrid pepper SHP9018 represents a new variety into which a new locus or trait may be introgressed. Direct transformation and backcrossing represent two important methods that can be used to accomplish such an introgression. The term backcross conversion and single locus conversion are used interchangeably to designate the product of a backcrossing program.

Molecular Techniques Using Hybrid Pepper SHP9018

The advent of new molecular biological techniques has allowed the isolation and characterization of genetic elements with specific functions, such as encoding specific protein products. Scientists in the field of plant biology developed a strong interest in engineering the genome of plants to contain and express foreign genetic elements, or additional, or modified versions of native or endogenous genetic elements in order to "alter" (the utilization of up-regulation, down-regulation, or gene silencing) the traits of a plant in a specific manner. Any DNA sequences, whether from a different species or from the same species, which are introduced into the genome using transformation or various breeding methods are referred to herein collectively as "transgenes." In some embodiments, a transgenic variant of hybrid pepper SHP9018 may contain at least one transgene. Over the last fifteen to twenty years several methods for producing transgenic plants have been developed, and another embodiment also relates to transgenic variants of the claimed hybrid pepper SHP9018.

Nucleic acids or polynucleotides refer to RNA or DNA that is linear or branched, single or double stranded, or a hybrid thereof. The term also encompasses RNA/DNA hybrids. These terms also encompass untranslated sequence located at both the 3' and 5' ends of the coding region of the gene: at least about 1000 nucleotides of sequence upstream from the 5' end of the coding region and at least about 200 nucleotides of sequence downstream from the 3' end of the coding region of the gene. Less common bases, such as inosine, 5-methylcytosine, 6-methyladenine, hypoxanthine and others can also be used for antisense, dsRNA and ribozyme pairing. For example, polynucleotides that contain C-5 propyne analogues of uridine and cytidine have been shown to bind RNA with high affinity and to be potent antisense inhibitors of gene expression. Other modifications, such as modification to the phosphodiester backbone, or the 2'-hydroxy in the ribose sugar group of the RNA can also be made. The antisense polynucleotides and ribozymes can consist entirely of ribonucleotides, or can contain mixed ribonucleotides and deoxyribonucleotides. The polynucleotides of the embodiments may be produced by any means, including genomic preparations, cDNA preparations, in-vitro synthesis, RT-PCR, and in vitro or in vivo transcription.

One embodiment is a process for producing hybrid pepper SHP9018 further comprising a desired trait, said process comprising introducing a transgene that confers a desired trait to a pepper plant of hybrid pepper SHP9018. Another embodiment is the product produced by this process. In one embodiment, the desired trait may be one or more of herbicide tolerance, insect tolerance, disease tolerance, environmental stress tolerance, or modified carbohydrate metabolism. The specific gene may be any known in the art or listed herein, including: a polynucleotide conferring resistance to imidazolinone, dicamba, sulfonylurea, glyphosate, glufosinate, triazine, PPO-inhibitor herbicides, benzonitrile, cyclohexanedione, phenoxy proprionic acid, and L-phosphinothricin; a polynucleotide encoding a *Bacillus thuringiensis* polypeptide; or a polynucleotide conferring resistance to Tomato spotted wilt virus, *Xanthomonas euvesicatoria*, *Bs*2, CARAV 1, or CaPME11.

Numerous methods for plant transformation have been developed, including biological and physical plant transformation protocols. See, for example, Li D. et al, "Establishment of a highly efficient transformation system for pepper (*Capsicum annuum* L.)" *Plant Cell Reports*, pp 785-788 (2003), and Lee Y. H. et al, "A new selection method for pepper transformation: callus-mediated shoot formation" *Plant Cell Reports* pp 50-58 (2004). In addition, expression vectors and in vitro culture methods for plant cell or tissue transformation and regeneration of plants are available. See, for example, Gruber, et al., "Vectors for Plant Transformation," in *Methods in Plant Molecular Biology and Biotechnology*, Glick and Thompson Eds., CRC Press, Inc., Boca Raton, pp. 89-119 (1993) and Nakagawa T. et al, "Development of series of gateway binary vectors, pGWBs, for realizing efficient construction of fusion genes for plant transformation" *Journal of Bioscience and Bioengineering* pp 34-41 (2007).

A genetic trait which has been engineered into the genome of a particular pepper plant may then be moved into the genome of another variety using traditional breeding techniques that are well known in the plant breeding arts. For example, a backcrossing approach is commonly used to move a transgene from a transformed hybrid pepper line into an already developed hybrid pepper line, and the resulting backcross conversion plant would then comprise the transgene(s).

Various genetic elements can be introduced into the plant genome using transformation. These elements include, but are not limited to, genes, coding sequences, inducible, constitutive and tissue specific promoters, enhancing sequences, and signal and targeting sequences. For example, see the traits, genes, and transformation methods listed in U.S. Pat. No. 6,118,055.

Breeding with Molecular Markers

Molecular markers, which includes markers identified through the use of techniques such as Isozyme Electrophoresis, Restriction Fragment Length Polymorphisms (RFLPs), Randomly Amplified Polymorphic DNAs (RAPDs), Amplified Fragment Length Polymorphisms (AFLPs), Arbitrarily Primed Polymerase Chain Reaction (AP-PCR), DNA Amplification Fingerprinting (DAF), Sequence Characterized Amplified Regions (SCARs), Simple Sequence Repeats (SSRs), and Single Nucleotide Polymorphisms (SNPs) may be used in plant breeding methods utilizing hybrid pepper SHP9018.

Isozyme Electrophoresis and RFLPs have been widely used to determine genetic composition. See Lee J. M et al, "Characterization and molecular genetic mapping of microsatellite loci in pepper" *Theoretical and Applied Genetics* pp 619-627 (2004), Kang B. C. et al, "An interspecific (*Capsicum annuum×C. Chinese*) F2 linkage map in pepper using RFLP and ALFP markers" *Theoretical and Applied Genetics* pp 531-539 (2001), and Lefebvre V. et al, "Nuclear RFLP between pepper cultivars (*Capsicum annuum* L.) *Euphytica* pp 189-199 (1993).

Randomly Amplified Polymorphic DNAs (RAPDs) and Amplified Fragment Length Polymorphisms (AFLPs) may also be used. See for example Paran, I. et al, "Variation in *Capsicum annuum* revealed by RAPD and AFLP markers" *Euphytica*, pp 167-173 (1998), and Llbi, H. "RAPD markers assisted varietal identification and genetic purity test in pepper, *Capsicum annuum*" *Scientia Horticulturae*, pp 211-218 (2003).

SSR technology can be routinely used. See Kwon, Y. et al, "Use of SSR Markers to Complement Tests of Distinctiveness, Uniformity, and Stability (DUS) of Pepper (*Capsicum annuum* L.) Varieties, *Mol. Cells*, pp 1-8 (2005) and Minamiyama, Y., et al "An SSR-based linkage map of *Capsicum annuum*" *Molecular Breeding*, pp 157-169 (2006).

Single Nucleotide Polymorphisms (SNPs) may also be used to identify the unique genetic composition of the embodiment(s) and progeny varieties retaining that unique genetic composition. See Jung, J. et al "Discovery of single nucleotide polymorphism in *Capsicum* and SNP markers for cultivar identification" *Euphytica* pp 91-107 (2010), Nicolai, M., et al "Discovery of a large set of SNP and SSR genetic markers by high-throughput sequencing of pepper (*Capsicum annuum*)" *Genetics and Molecular Research*, pp 2295-2300 (2012), Jeong, H. et al, "Identification of *Capsicum* species using SNP markers based on high resolution melting analysis" *Genome* pp 1029-1040 (2010), and Ashrafi, H., et al, "De novo assembly of the pepper transcriptome (*Capsicum annuum*): a benchmark for in silico discovery of SNPs, SSRs and candidate genes" *BMC Genomics* (2012).

One use of molecular markers is Quantitative Trait Loci (QTL) mapping. QTL mapping is the use of markers, which are known to be closely linked to alleles that have measurable effects on a quantitative trait. Selection in the breeding process is based upon the accumulation of markers linked to the positive effecting alleles and/or the elimination of the markers linked to the negative effecting alleles from the plant's genome. See Chaim, A. B., et al, "QTL mapping of fruit-related traits in pepper (*Capsicum annuum*), *Theoretical and Applied Genetics*, pp 1016-1028 (2001) and Rao, G. U., et al, "Mapping of yield-related QTLs in pepper in an interspecific cross of *Capsicum annuum* and *C. frutescens*" *Theoretical and Applied Genetics*, pp 1457-1466 (2003). QTL markers can also be used during the breeding process for the selection of qualitative traits. For example, markers closely linked to alleles or markers containing sequences within the actual alleles of interest can be used to select plants that contain the alleles of interest during a backcrossing breeding program. The markers can also be used to select for the genome of the recurrent parent and against the genome of the donor parent. Using this procedure can minimize the amount of genome from the donor parent that remains in the selected plants. It can also be used to reduce the number of crosses back to the recurrent parent needed in a backcrossing program. The use of molecular markers in the selection process is often called genetic marker enhanced selection. Molecular markers may also be used to identify and exclude certain sources of germplasm as parental varieties or ancestors of a plant by providing a means of tracking genetic profiles through crosses.

Production of Double Haploids

The production of double haploids can also be used for the development of plants with a homozygous phenotype in the breeding program. For example, a pepper plant for which hybrid pepper SHP9018 is a parent can be used to produce double haploid plants. Double haploids are produced by the doubling of a set of chromosomes (1N) from a heterozygous plant to produce a completely homozygous individual. This can be advantageous because the process omits the generations of selfing needed to obtain a homozygous plant from a heterozygous source. For example, see Kele, D. et al, "Effect of Pepper Types on Obtaining Spontaneous Doubled Haploid Plants via Anther culture" *HortScience*, pp1671-1676 (2015), Olszewska, D. et al, "The assessment of doubled haploid lines obtained in pepper (*Capsicum annuum* L.) anther culture" *Folia Horticulturae*, pp 93-99 (2011), and M. Maluszynski et al. (eds), *Doubled Haploid Production in Crop Plants*, (2003).

Thus, an embodiment is a process for making a substantially homozygous hybrid pepper SHP9018 progeny plant by producing or obtaining a seed from the cross of hybrid pepper SHP9018 and another pepper plant and applying double haploid methods to the $F_1$ seed or $F_1$ plant or to any successive filial generation.

In particular, a process of making seed retaining the molecular marker profile of hybrid pepper SHP9018 is contemplated, such process comprising obtaining or producing $F_1$ seed for which hybrid pepper SHP9018 is a parent, inducing doubled haploids to create progeny without the occurrence of meiotic segregation, obtaining the molecular marker profile of hybrid pepper SHP9018, and selecting progeny that retain the molecular marker profile of hybrid pepper SHP9018.

Expression Vectors for Pepper Transformation: Marker Genes

Plant transformation involves the construction of an expression vector which will function in plant cells. Such a vector comprises DNA comprising a gene under control of, or operatively linked to, a regulatory element (for example, a promoter). Expression vectors include at least one genetic marker operably linked to a regulatory element (for example, a promoter) that allows transformed cells containing the marker to be either recovered by negative selection, i.e., inhibiting growth of cells that do not contain the selectable marker gene, or by positive selection, i.e., screening for the product encoded by the genetic marker. Many commonly used selectable marker genes for plant transformation are well-known in the transformation arts, and include, for example, genes that code for enzymes that metabolically detoxify a selective chemical agent which may be an antibiotic or an herbicide, or genes that encode an altered target which is insensitive to the inhibitor. A few positive selection methods are also known in the art.

One commonly used selectable marker gene for plant transformation is the neomycin phosphotransferase II (nptII) gene which, when under the control of plant regulatory signals, confers resistance to kanamycin. Another commonly used selectable marker gene is the hygromycin phosphotransferase gene which confers resistance to the antibiotic hygromycin.

Additional selectable marker genes include Pain1-9a and Pain1-8c which both correspond to the group a alleles of the vacuolar acid invertase gene; Pain1prom-d/e; Stp23-8b, StpL-3b, and StpL-3e which originate from two plastid starch phosphorylase genes; AGPsS-9a which is positively associated an increase in plant starch content, starch yield and chip quality, and AGPsS-10a which is associated with a decrease in the average plant starch content, starch yield and chip quality; GP 171-a which corresponds to allele 1a of ribulose bisphosphate carboxylase activase; and Rca-1a.

Selectable marker genes for plant transformation not of bacterial origin include, for example, mouse dihydrofolate reductase, plant 5-enolpyruvylshikimate-3-phosphate synthase, and plant acetolactate synthase (Eichholtz, et al., *Somatic Cell Mol. Genet.*, 13:67 (1987); Shah, et al., *Science*, 233:478 (1986); Charest, et al., *Plant Cell Rep.*, 8:643 (1990)).

Another class of marker genes for plant transformation requires screening of presumptively transformed plant cells, rather than direct genetic selection of transformed cells, for resistance to a toxic substance such as an antibiotic. These genes are particularly useful to quantify or visualize the spatial pattern of expression of a gene in specific tissues and are frequently referred to as reporter genes because they can be fused to a gene or gene regulatory sequence for the investigation of gene expression. Commonly used marker genes for screening presumptively transformed cells include β-glucuronidase (GUS), β-galactosidase, luciferase, and chloramphenicol acetyltransferase (Jefferson, R. A., *Plant Mol. Biol. Rep.*, 5:387 (1987); Teeri, et al., *EMBO J.*, 8:343 (1989); Koncz, et al., *Proc. Natl. Acad. Sci. USA*, 84:131 (1987); DeBlock, et al., *EMBO J.*, 3:1681 (1984)).

Expression Vectors for Pepper Transformation: Promoters

Genes included in expression vectors must be driven by a nucleotide sequence comprising a regulatory element (for example, a promoter). Several types of promoters are well known in the transformation arts as are other regulatory elements that can be used alone or in combination with promoters.

As used herein, "promoter" includes reference to a region of DNA upstream from the start of transcription and involved in recognition and binding of RNA polymerase and other proteins to initiate transcription. A "plant promoter" is a promoter capable of initiating transcription in plant cells. Examples of promoters under developmental control include promoters that preferentially initiate transcription in certain tissues, such as leaves, roots, seeds, fibers, xylem vessels, tracheids, or sclerenchyma. Such promoters are referred to as "tissue-preferred." Promoters that initiate transcription only in a certain tissue are referred to as "tissue-specific." A "cell-type" specific promoter primarily drives expression in certain cell types in one or more organs, for example, vascular cells in roots or leaves. An "inducible" promoter is a promoter which is under environmental control. Examples of environmental conditions that may affect transcription by inducible promoters include anaerobic conditions or the presence of light. Tissue-specific, tissue-preferred, cell-type specific, and inducible promoters constitute the class of "non-constitutive" promoters. A "constitutive" promoter is a promoter that is active under most environmental conditions. Many types of promoters are well known in the art.

Signal Sequences for Targeting Proteins to Subcellular Compartments

Transport of a protein produced by transgenes to a subcellular compartment, such as the chloroplast, vacuole, peroxisome, glyoxysome, cell wall, or mitochondrion, or for secretion into the apoplast, is accomplished by means of operably linking the nucleotide sequence encoding a signal sequence to the 5' and/or 3' region of a gene encoding the protein of interest. Targeting sequences at the 5' and/or 3' end of the structural gene may determine during protein synthesis and processing where the encoded protein is ultimately compartmentalized. Many signal sequences are well-known in the art. See, for example, Becker, et al., *Plant Mol. Biol.,* 20:49 (1992); Knox, C., et al., *Plant Mol. Biol.,* 9:3-17 (1987); Lerner, et al., *Plant Physiol.,* 91:124-129 (1989); Frontes, et al., *Plant Cell,* 3:483-496 (1991); Matsuoka, et al., *Proc. Natl. Acad. Sci.,* 88:834 (1991); Gould, et al., *J. Cell. Biol.,* 108:1657 (1989); Creissen, et al., *Plant 1,* 2:129 (1991); Kalderon, et al., *Cell,* 39:499-509 (1984); Steifel, et al., *Plant Cell,* 2:785-793 (1990).

Foreign Protein Genes and Agronomic Genes: Transformation

With transgenic plants, according to one embodiment, a foreign protein can be produced in commercial quantities. Thus, techniques for the selection and propagation of transformed plants, which are well understood in the art, yield a plurality of transgenic plants which are harvested in a conventional manner, and a foreign protein can then be extracted from a tissue of interest or from total biomass. Protein extraction from plant biomass can be accomplished by known methods which are discussed, for example, by Heney and Orr, *Anal. Biochem.,* 114:92-6 (1981).

According to an embodiment, the transgenic plant provided for commercial production of foreign protein is a pepper plant. In another embodiment, the biomass of interest is seed. For the relatively small number of transgenic plants that show higher levels of expression, a genetic map can be generated, primarily via conventional RFLP, PCR, and SSR analysis, which identifies the approximate chromosomal location of the integrated DNA molecule. For exemplary methodologies in this regard, see, Glick and Thompson, *Methods in Plant Molecular Biology and Biotechnology,* CRC Press, Inc., Boca Raton, 269:284 (1993). Map information concerning chromosomal location is useful for proprietary protection of a subject transgenic plant.

Likewise, by means of one embodiment, plants can be genetically engineered to express various phenotypes of agronomic interest. Through the transformation of pepper, the expression of genes can be altered to enhance disease tolerance, insect tolerance, herbicide tolerance, agronomic, grain quality, and other traits. Transformation can also be used to insert DNA sequences which control or help control male-sterility. DNA sequences native to peppers, as well as non-native DNA sequences, can be transformed into peppers and used to alter levels of native or non-native proteins. Various promoters, targeting sequences, enhancing sequences, and other DNA sequences can be inserted into the genome for the purpose of altering the expression of proteins. The interruption or suppression of the expression of a gene at the level of transcription or translation (also known as gene silencing or gene suppression) is desirable for several aspects of genetic engineering in plants.

Many techniques for gene silencing are well-known to one of skill in the art, including, but not limited to, knock-outs (such as by insertion of a transposable element such as Mu (Vicki Chandler, *The Maize Handbook,* Ch. 118 (Springer-Verlag 1994)) or other genetic elements such as a FRT, Lox, or other site specific integration sites; antisense technology (see, e.g., Sheehy, et al., *PNAS USA,* 85:8805-8809 (1988) and U.S. Pat. Nos. 5,107,065, 5,453,566, and 5,759,829); co-suppression (e.g., Taylor, *Plant Cell,* 9:1245 (1997); Jorgensen, *Trends Biotech.,* 8(12):340-344 (1990); Flavell, *PNAS USA,* 91:3490-3496 (1994); Finnegan, et al., *Bio/Technology,* 12:883-888 (1994); Neuhuber, et al., *Mol. Gen. Genet.,* 244:230-241 (1994)); RNA interference (Napoli, et al., *Plant Cell,* 2:279-289 (1990); U.S. Pat. No. 5,034,323; Sharp, *Genes Dev.,* 13:139-141 (1999); Zamore, et al., *Cell,* 101:25-33 (2000); Montgomery, et al., *PNAS USA,* 95:15502-15507 (1998)), virus-induced gene silencing (Burton, et al., *Plant Cell,* 12:691-705 (2000); Baulcombe, *Curr. Op. Plant Bio.,* 2:109-113 (1999)); target-RNA-specific ribozymes (Haseloff, et al., *Nature,* 334:585-591 (1988)); hairpin structures (Smith, et al., *Nature,* 407:319-320 (2000); U.S. Pat. Nos. 6,423,885, 7,138,565, 6,753,139, and 7,713,715); MicroRNA (Aukerman & Sakai, *Plant Cell,* 15:2730-2741 (2003)); ribozymes (Steinecke, et al., *EMBO J.,* 11:1525 (1992); Perriman, et al., *Antisense Res. Dev.,* 3:253 (1993)); oligonucleotide mediated targeted modification (e.g., U.S. Pat. Nos. 6,528,700 and 6,911,575); Zn-finger targeted molecules (e.g., U.S. Pat. Nos. 7,151,201, 6,453,242, 6,785,613, 7,177,766 and 7,788,044); and other methods or combinations of the above methods known to those of skill in the art.

The foregoing methods for transformation may be used for producing a transgenic variety. The transgenic variety could then be crossed with another (non-transformed or transformed) variety in order to produce a new transgenic variety. Alternatively, a genetic trait that has been engineered into a particular pepper line using the foregoing transformation techniques could be moved into another line using traditional backcrossing techniques that are well known in the plant breeding arts. For example, a backcrossing approach could be used to move an engineered trait from a public, non-elite variety into an elite variety, or from a variety containing a foreign gene in its genome into a variety or varieties that do not contain that gene. As used herein, "crossing" can refer to a simple x by y cross or the process of backcrossing depending on the context.

Likewise, by means of one embodiment, agronomic genes can be expressed in transformed plants. More particularly, plants can be genetically engineered to express various phenotypes of agronomic interest, including, but not limited to, genes that confer resistance to pests or disease, genes that confer resistance to an herbicide, genes that confer or contribute to a value-added or desired trait, genes that control male sterility, genes that create a site for site specific DNA integration, and genes that affect abiotic stress resistance. Many hundreds if not thousands of different genes are known and could potentially be introduced into a pepper plant according to the invention. Non-limiting examples of particular genes and corresponding phenotypes one may choose to introduce into a pepper plant include one or more genes for insect tolerance, such as a *Bacillus thuringiensis* (B.t.) gene, pest tolerance such as genes for fungal disease control, herbicide tolerance such as genes conferring glyphosate tolerance, and genes for quality improvements such as yield, nutritional enhancements, environmental or stress tolerances, or any desirable changes in plant physiology, growth, development, morphology or plant product(s). For example, structural genes would include any gene that confers insect tolerance including but not limited to a *Bacillus* insect control protein gene as described in WO 99/31248, herein incorporated by reference in its entirety, U.S. Pat. No. 5,689,052, herein incorporated by reference in its entirety, U.S. Pat. Nos. 5,500,365 and 5,880,275, herein incorporated by reference in their entirety. In another embodiment, the structural gene can confer tolerance to the herbicide glyphosate as conferred by genes including, but not limited to *Agrobacterium* strain CP4 glyphosate resistant EPSPS gene (aroA:CP4) as described in U.S. Pat. No. 5,633,435, herein incorporated by reference in its entirety, or glyphosate oxidoreductase gene (GOX) as described in U.S. Pat. No. 5,463,175, herein incorporated by reference in its entirety. Alternatively, the DNA coding sequences can affect these phenotypes by encoding a non-translatable RNA molecule that causes the targeted inhibition of expression of an endogenous gene, for example via antisense- or cosuppression-mediated mechanisms (see, for example, Bird et al., *Biotech. Gen. Engin. Rev.*, 9:207, 1991). The RNA could also be a catalytic RNA molecule (i.e., a ribozyme) engineered to cleave a desired endogenous mRNA product (see for example, Gibson and Shillito, *Mol. Biotech.*, 7:125, 1997). Thus, any gene which produces a protein or mRNA which expresses a phenotype or morphology change of interest is useful for the practice of one or more embodiments.

Tissue Culture

Further reproduction of the variety can occur by tissue culture and regeneration. Tissue culture of various tissues of peppers and regeneration of plants therefrom is well-known and widely published. See, Agrawal, S. et al., "Plant regeneration in tissue cultures of pepper (*Capsicum annuum* L. cv. *Mathania*) *Plant Cell, Tissue and Organ Culture*, Vol. 16(1) pp 47-55 1989; Berljak J. "In vitro plant regeneration from Pepper (*Capsicum annuum* L. cv. 'Soroksari') Seedling Explants" *Phyton (Austria) Special issue: "Plant Physiology"* Vol. 39(3) pp 289-292 (1999); Ahmad, N., et al., "Improved plant regeneration in *Capsicum annuum* L. from nodal segments" *Biologia Plantarum* Vol. 50(4) pp 701-704 (2006); and Otroshy, M. et al., "Micropropagation of Pepper (*Capsicum annuum* L.) Through in vitro Direct Organogenesis" *Asian Journal of Biotechnology* Vol. 3 pp 38-45 (2010). Thus, another aspect or embodiment is to provide cells which upon growth and differentiation produce pepper plants having the physiological and morphological characteristics of hybrid pepper SHP9018.

Regeneration refers to the development of a plant from tissue culture. The term "tissue culture" indicates a composition comprising isolated cells of the same or a different type or a collection of such cells organized into parts of a plant. Exemplary types of tissue cultures are protoplasts, calli, plant clumps, and plant cells that can generate tissue culture that are intact in plants or parts of plants, such as embryos, pollen, flowers, seeds, pods, petioles, leaves, stems, roots, root tips, anthers, pistils, and the like. Means for preparing and maintaining plant tissue culture are well known in the art. By way of example, a tissue culture comprising organs has been used to produce regenerated plants. U.S. Pat. Nos. 5,959,185, 5,973,234, and 5,977,445 describe certain techniques, the disclosures of which are incorporated herein by reference.

Industrial Uses

Pepper has a wide variety of uses in the commodity area. For example, fresh peppers can be eaten raw or cooked (fried, baked, boiled, etc). Peppers can also be used to make spices. Thus, a further embodiment provides for a food product made from a part of the pepper plant variety SHP9018.

In addition to the exemplary aspects and embodiments described above, further aspects and embodiments will become apparent by study of the following descriptions.

While a number of exemplary aspects and embodiments have been discussed above, those of skill in the art will recognize certain modifications, permutations, additions and sub-combinations thereof. It is therefore intended that the following appended claims and claims hereafter introduced are interpreted to include all such modifications, permutations, additions, and sub-combinations as are within their true spirit and scope.

One embodiment may be embodied in other specific forms without departing from its spirit or essential characteristics. The described embodiments are to be considered in all respects only as illustrative and not restrictive. All changes which come within the meaning and range of equivalency of the claims are to be embraced within their scope.

Various embodiments, include components, methods, processes, systems and/or apparatus substantially as depicted and described herein, including various embodiments, sub-combinations, and subsets thereof. Those of skill in the art will understand how to make and use an embodiment(s) after understanding the present disclosure.

The foregoing discussion of the embodiments has been presented for purposes of illustration and description. The foregoing is not intended to limit the embodiments to the form or forms disclosed herein. In the foregoing Detailed Description for example, various features of the embodiments are grouped together in one or more embodiments for the purpose of streamlining the disclosure. This method of disclosure is not to be interpreted as reflecting an intention that the embodiment(s) requires more features than are expressly recited in each claim. Rather, as the following claims reflect, inventive aspects lie in less than all features of a single foregoing disclosed embodiment. Thus, the following claims are hereby incorporated into the detailed description.

Moreover, though the description of the embodiments has included description of one or more embodiments and certain variations and modifications, other variations and modifications are within the scope of the embodiments (e.g., as may be within the skill and knowledge of those in the art, after understanding the present disclosure). It is intended to obtain rights which include alternative embodiments to the extent permitted, including alternate, interchangeable and/or equivalent structures, functions, ranges or acts to those claimed, whether or not such alternate, interchangeable and/or equivalent structures, functions, ranges or acts are disclosed herein, and without intending to publicly dedicate any patentable subject matter.

The use of the terms "a," "an," and "the," and similar referents in the context of describing the embodiments (especially in the context of the following claims) are to be construed to cover both the singular and the plural, unless otherwise indicated herein or clearly contradicted by context. The terms "comprising," "having," "including," and "containing" are to be construed as open-ended terms (i.e., meaning "including, but not limited to,") unless otherwise noted. Recitation of ranges of values herein are merely intended to serve as a shorthand method of referring individually to each separate value falling within the range, unless otherwise indicated herein, and each separate value is incorporated into the specification as if it were individually recited herein. For example, if the range 10-15 is disclosed, then 11, 12, 13, and 14 are also disclosed. All methods described herein can be performed in any suitable order unless otherwise indicated herein or otherwise clearly contradicted by context. The use of any and all examples, or exemplary language (e.g., "such as") provided herein, is intended merely to better illuminate the embodiments and does not pose a limitation on the scope of the embodiments unless otherwise claimed.

DEPOSIT INFORMATION

A deposit of the Sakata Seed America, Inc. proprietary pasilla pepper SHP9018 seed disclosed above and recited in the appended claims has been made with the Provasoli-Guillard National Center for Marine Algae and Microbiota, Bigelow Laboratory for Ocean Sciences (NCMA), 60 Bigelow Drive, East Boothbay, Me. 04544. The date of deposit was Dec. 24, 2019. The NCMA No. is 202012122. The deposit of at least 625 seeds was taken from the same deposit maintained by Sakata Seed America, Inc. since prior to the filing date of this application. The deposit will be maintained in the NCMA depository for a period of 30 years, or 5 years after the most recent request, or for the enforceable life of the patent, whichever is longer, and will be replaced if necessary, during that period. Upon issuance, all restrictions on the availability to the public of the deposit will be irrevocably removed consistent with all of the requirements of 37 C.F.R. §§ 1.801-1.809.

What is claimed is:

1. A seed of hybrid pepper plant designated SHP9018, a sample of seed of said hybrid pepper SHP9018 having been deposited under NCMA No. 202012122.

2. A pepper plant produced from the seed of claim 1.

3. A plant part of the plant of claim 2, wherein said part is a cell, pollen, leaf, ovule, anther, cotyledon, hypocotyl, pistil, root, root tip, flower, fruit, petiole, or stem.

4. A tissue culture produced from protoplasts or cells from the plant of claim 2, wherein said cells or protoplasts are produced from a plant part selected from the group consisting of leaf, pollen, ovule, cotyledon, hypocotyl, meristematic cell, callus, root, root tip, pistil, anther, flower, fruit, shoot, stem, and petiole.

5. A pepper plant produced from the tissue culture of claim 4, having essentially all of the physiological and morphological characteristics of hybrid pepper SHP9018.

6. A method of vegetatively propagating the pepper plant of claim 2, said method comprising the steps of:
(a) collecting tissue capable of being propagated from the plant according to claim 2;
(b) cultivating said tissue to obtain proliferated shoots; and
(c) rooting said proliferated shoots to obtain rooted plantlets.

7. The method of claim 6, further comprising growing at least a first pepper plant from said rooted plantlets.

8. A method of producing a pepper plant comprising a desired trait, the method comprising introducing a transgene conferring the trait into the plant of claim 2.

9. A pepper plant produced by the method of claim 8.

10. The plant of claim 9, wherein the transgene confers a trait selected from the group consisting of male sterility, herbicide tolerance, insect tolerance, pest tolerance, disease tolerance, modified fatty acid metabolism, environmental stress tolerance, and modified carbohydrate metabolism.

11. The plant of claim 9, wherein the trait is herbicide tolerance and wherein said herbicide tolerance is conferred to an herbicide selected from the group consisting of imidazolinone, sulfonylurea, glyphosate, glufosinate, L-phosphinothricin, triazine and benzonitrile.

12. The plant of claim 9, wherein the trait is insect tolerance and wherein said insect tolerance is conferred by a transgene encoding a *Bacillus thuringiensis* endotoxin.

13. A method for producing a seed of a pepper plant derived from pepper hybrid SHP9018, said method comprising the steps of:
(a) crossing a pepper plant of hybrid SHP9018 with itself or a second pepper plant, a sample of seed of said hybrid having been deposited under NCMA No. 202012122; and
(b) allowing seed of a hybrid SHP9018-derived pepper plant to form.

14. The method of claim 13, further comprising the steps of:
(c) selfing a plant grown from said hybrid SHP9018-derived pepper seed to yield additional hybrid SHP9018-derived pepper seed;
(d) growing said additional hybrid SHP9018-derived pepper seed of step (c) to yield additional hybrid SHP9018-derived pepper plants; and
(e) repeating the selfing and growing steps of (c) and (d) to generate at least a first further hybrid SHP9018-derived pepper plant.

15. The method of claim 14, further comprising:
(f) crossing the further hybrid SHP9018-derived pepper plant with a second pepper plant to produce seed of a hybrid progeny plant.

16. A method of producing a pepper fruit, said method comprising:
(a) obtaining the plant according to claim 2, wherein the plant has been cultivated to maturity; and
(b) collecting a pepper fruit from said plant.

17. The method of claim 14, wherein said second pepper plant is an inbred pepper line.

18. A plant part of the plant of claim 2, wherein the plant part comprises a cell of said hybrid pepper SHP9018.

19. A method for developing a pepper plant in a plant breeding program, said method comprising applying plant breeding techniques to the plant, or plant part thereof, of claim 2, comprising crossing, recurrent selection, mutation breeding, wherein said mutation breeding selects for a mutation that is spontaneous or artificially induced, backcrossing, pedigree breeding, marker enhanced selection, haploid/double haploid production, or transformation to the pepper plant of claim 2, or its parts, wherein application of said techniques results in development of a pepper plant.

20. A method of introducing a mutation into the genome of pepper plant SHP9018, said method comprising mutagenesis of the plant, or plant part thereof, of claim 2, wherein said mutagenesis is selected from the group consisting of temperature, long-term seed storage, tissue culture conditions, ionizing radiation, chemical mutagens, or targeting induced local lesions in genomes, and wherein the resulting plant comprises at least one genome mutation.

21. A method of editing the genome of pepper plant SHP9018, said method comprising editing the genome of the plant, or plant part thereof, of claim 2, wherein said method is selected from the group comprising zinc finger nucleases, transcription activator-like effector nucleases (TALENs), engineered homing endonucleases/meganucleases, and the clustered regularly interspaced short palindromic repeat (CRISPR)-associated protein9 (Cas9) system.

22. A pepper plant produced by the method of claim 21, wherein said plant otherwise has all of the morphological and physiological characteristics of pepper plant SHP9018.

* * * * *